(12) United States Patent
Perriello et al.

(10) Patent No.: US 7,966,767 B2
(45) Date of Patent: Jun. 28, 2011

(54) ENHANCED PLANT GROWTH USING ALKANE BIOSTIMULATION

(75) Inventors: Felix Anthony Perriello, Norwood, MA (US); George A. DiCesare, Norwood, MA (US); Jeanne M. Perriello, Norwood, MA (US)

(73) Assignee: Global BioSciences, Inc., North Attleborough, MA (US)

( * ) Notice: Subject to any disclaimer, the term of this patent is extended or adjusted under 35 U.S.C. 154(b) by 2139 days.

(21) Appl. No.: 10/282,891

(22) Filed: Oct. 29, 2002

(65) Prior Publication Data

US 2003/0084609 A1 May 8, 2003

Related U.S. Application Data

(60) Provisional application No. 60/334,981, filed on Oct. 31, 2001.

(51) Int. Cl.
*A01G 7/00* (2006.01)
*A01B 79/02* (2006.01)

(52) U.S. Cl. ................. 47/58.1 SC; 47/58.1 R
(58) Field of Classification Search ............ 47/58.112, 47/58.15 C; 111/118, 119
See application file for complete search history.

(56) References Cited

U.S. PATENT DOCUMENTS

| | | | |
|---|---|---|---|
| 3,183,171 A * | 5/1965 | Schreiner | 435/244 |
| 3,184,891 A | 5/1965 | Frantzen | |
| 3,185,117 A * | 5/1965 | Frantzen | 111/124 |
| 3,361,555 A | 1/1968 | Herschler | |
| 3,372,658 A * | 3/1968 | Ammann | 111/119 |
| 3,474,001 A | 10/1969 | Leavitt | |
| 3,550,319 A * | 12/1970 | Gainers, Jr. | 47/79 |
| 3,661,549 A | 5/1972 | Freytag et al. | |
| 3,813,290 A | 5/1974 | Heilweil et al. | |
| 4,119,429 A | 10/1978 | Lovness | |
| 4,321,142 A | 3/1982 | Starr | |
| RE31,924 E | 6/1985 | Starr | |
| 4,713,343 A | 12/1987 | Wilson, Jr. et al. | |

(Continued)

FOREIGN PATENT DOCUMENTS

WO    WO 03037066 A2 *  5/2003

OTHER PUBLICATIONS

Todar.2002. *Pseudomonas aeruginosa.* at hhttp://www.bact.wisc.edu/Bact330/lecturepseudomonas.*

(Continued)

*Primary Examiner* — Son T. Nguyen
(74) *Attorney, Agent, or Firm* — Alan G. Towner, Esq.; Pietragallo Gordon Alfano Bosick & Raspanti, LLP

(57) ABSTRACT

A method of enhancing plant growth comprises the step of introducing an alkane into a location adjacent to a plant. The alkane can be introduced intermittently, and can be combined with another gas and/or nutrients. The alkane preferably comprises a butane substrate. The butane substrate can stimulate the growth of butane-utilizing bacteria, such as *Aeromonas caviae, Stenotrophomonas maltophilia, Micrococcus varians, Aureobacterium esteroaromaticum, Aureobacterium barkeri, Rhodococcus fascians, Nocardia paradoxus, Comamonas acidovorans* and *Pseudomonas aeruginosa.* The alkane can increase the amount of heterotrophic bacteria in the location adjacent to the plant, and thereby accelerate a heterotrophic nitrification process. The butane substrate can also stimulate the growth of butane-utilizing fungi. The method can also enhance the growth protists and/or prokaryotes. A system for enhancing plant growth in accordance with the method is also disclosed.

65 Claims, 11 Drawing Sheets

U.S. PATENT DOCUMENTS

| | | |
|---|---|---|
| 5,147,441 A | 9/1992 | Megeed |
| 5,266,096 A | 11/1993 | Slavensky |
| 5,441,885 A * | 8/1995 | Goldberg et al. ........ 435/252.34 |
| 5,697,186 A | 12/1997 | Neyra et al. |
| 5,733,355 A | 3/1998 | Hibino et al. |
| 5,802,996 A * | 9/1998 | Baxter .......................... 111/118 |
| 5,888,396 A | 3/1999 | Perriello |
| 5,951,978 A | 9/1999 | Red'kina |
| 6,051,130 A | 4/2000 | Perriello |
| 6,105,309 A | 8/2000 | Takayanagi |
| 6,110,372 A | 8/2000 | Perriello |
| 6,156,203 A | 12/2000 | Anthony |
| 6,194,193 B1 | 2/2001 | Drahos et al. |
| 6,210,579 B1 | 4/2001 | Perriello |
| 6,244,346 B1 | 6/2001 | Perriello |
| 6,245,235 B1 | 6/2001 | Perriello |
| 6,488,850 B2 | 12/2002 | Perriello |
| 2003/0041515 A1 * | 3/2003 | Layzell et al. ........... 47/58.1 SC |
| 2003/0084609 A1 * | 5/2003 | Perriello et al. ......... 47/58.1 SC |
| 2003/0167686 A1 * | 9/2003 | Perriello .................. 47/58.1 SC |

OTHER PUBLICATIONS

N. Hamamura et al., "Diversity in Butane Monooxygenases Among Butane-Grown Bacteria," *Applied and Environmental Microbiology*, vol. 65, No. 10, Oct. 1999, pp. 4586-4593.

Toccalino et al., "Nitrogen Limitation and Nitrogen Fixation during Alkane Biodegradation in a Sandy Soil," *Applied and Environmental Microbiology*, Sep. 1993; p. 2977-2983, vol. 59, No. 9.

\* cited by examiner

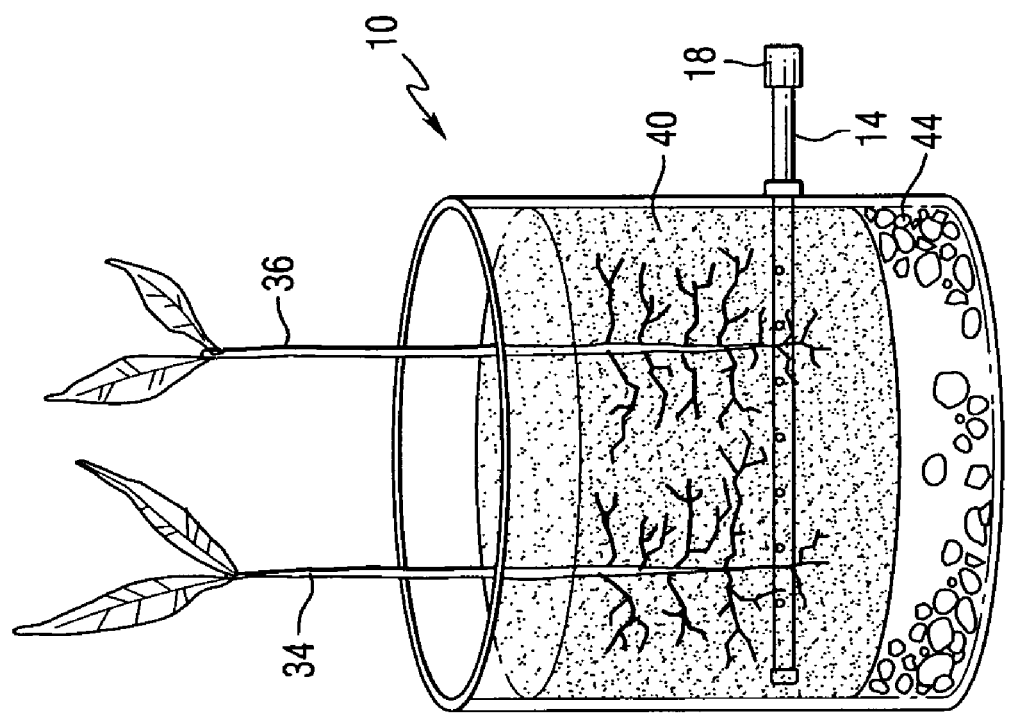
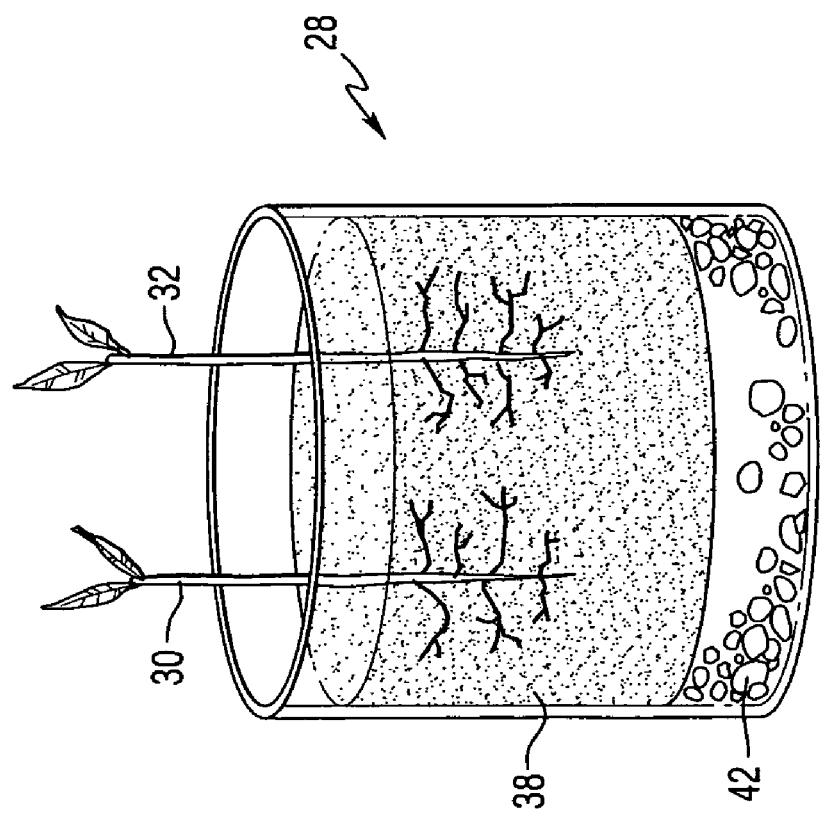
FIG. 3

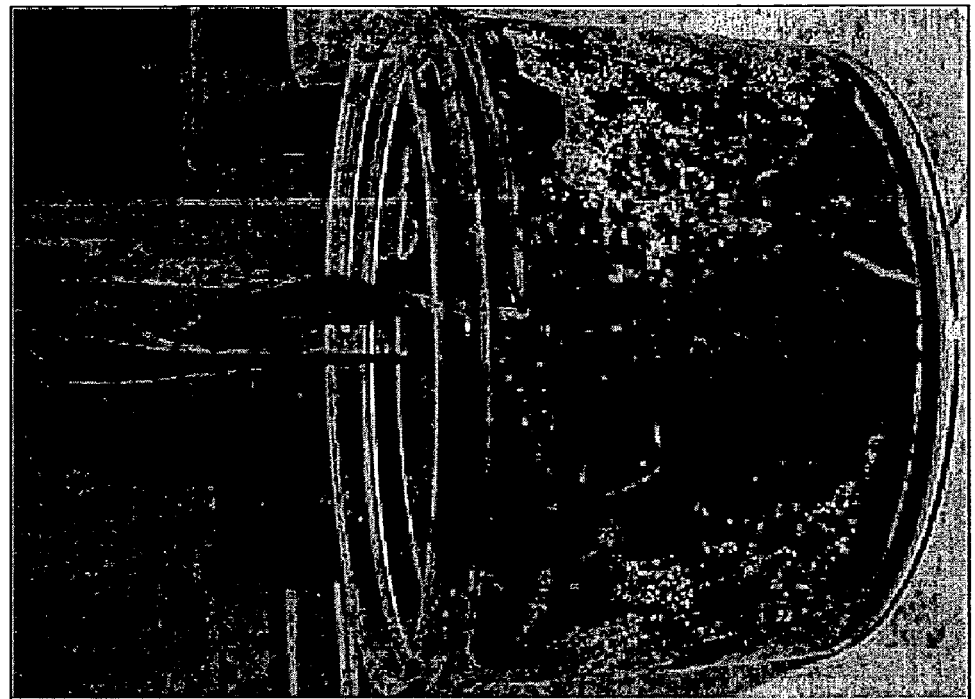
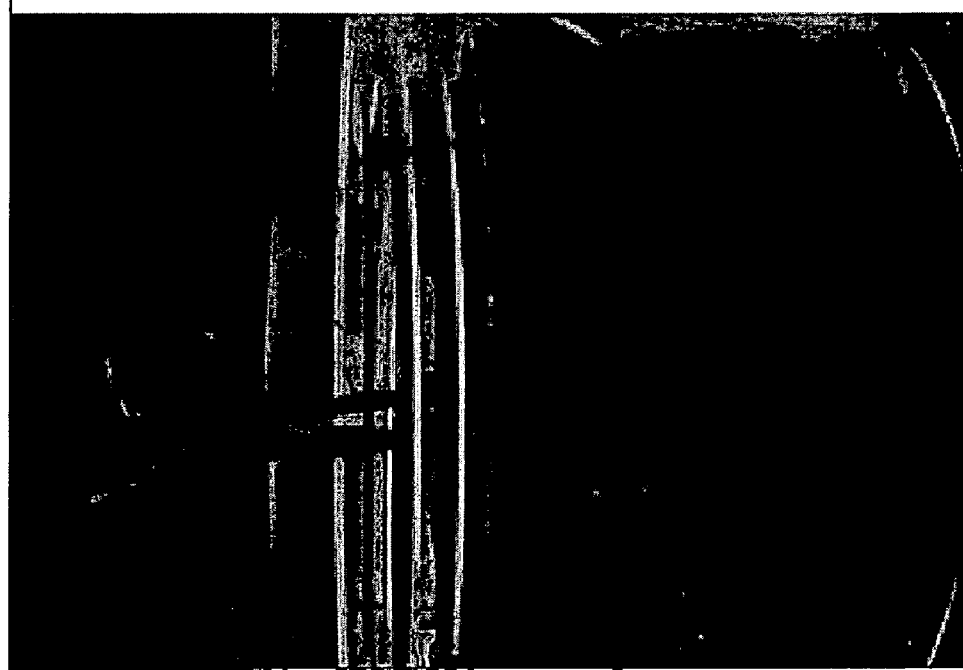
EXAMPLE 1
ROOT GROWTH IN VESSEL
CONTROL
BUTANE ENHANCED
FIG. 5

EXAMPLE 2
SEEDLING GROWTH COMPARISON

BUTANE ENHANCED     CONTROL

EXAMPLE 2
CONTROL ROOT GROWTH

EXAMPLE 2
BUTANE ENHANCED ROOT GROWTH

EXAMPLE 2
ROOT GROWTH COMPARISON
CONTROL
BUTANE ENHANCED

ENHANCED PLANT GROWTH USING ALKANE BIOSTIMULATION

CROSS-REFERENCE TO RELATED APPLICATION

This application claims the benefit of U.S. Provisional Patent Application Ser. No. 60/334,981, filed Oct. 31, 2001.

FIELD OF THE INVENTION

The present invention provides enhanced plant growth. More particularly, the invention provides methods and apparatus for using alkanes, such as butane, in order to stimulate plant growth.

BACKGROUND INFORMATION

Soil systems contain a variety of microorganisms including bacteria, fungi and algae. Bacterial populations in soil survive and flourish depending on the availability of nutrients and carbon sources. Aerated soils including topsoil typically have the highest population of bacteria. A level of population for each type of bacteria in soil is defined based on the competition among soil bacteria. Competition may be shifted toward a specific type of bacteria due to changes in the availability of growth requirements as well as changes resulting in the alteration of physical or chemical conditions within the subsurface environment. The addition or natural presence of a carbon source becomes a major element affecting the bacterial diversity in an ecosystem. Fungi live in symbiotic relationships with plants among their roots, feeding on organic materials and assisting plants in water and mineral uptake. A number of genera of algae live both on the soil surface and within the soil, where they produce oxygen used by aerobes and serve as a food source for other microorganisms.

Commercial growers have access to inoculant products that add specific beneficial fungi and bacteria to a soil mix, growing bed or crop. It is reported by some that these microorganisms help prevent disease, increase plants' tolerance to stress and increase their vigor. Some farmers and crop growers have claimed that these products even increase plants' cold tolerance. These products are available as a powder to mix with water and add to soils, or as granular material that is mixed with water and added to soil. Some of these products are mixed with nutrients that also increase the number of existing microorganisms.

In general, bacteria-based products are lower in cost than fungal-based products or enhancers. Both the bacterial products and fungal products are designed to increase nutrient uptake, promote faster root development, and reduce heat, drought and cold stress. These products also stimulate other beneficial soil microorganisms to thrive. Thus, these commercial products increase overall crop health, even those crops grown in soil-less media or in soil that has become exhausted and overworked. However, soil based amendments applied through inoculation methods may not be reliable.

SUMMARY OF THE INVENTION

A method of enhancing plant growth comprises the step of introducing an alkane into a location adjacent to a plant. The alkane can be introduced intermittently, and can be combined with another gas and/or nutrients. The alkane preferably comprises a butane substrate. The butane substrate can stimulate the growth of butane-utilizing bacteria, such as *Aeromonas caviae, Stenotrophomonas maltophilia, Micrococcus varians, Aureobacterium esteroaromaticum, Aureobacterium barkeri, Rhodococcus fascians, Nocardia paradoxus, Comamonas acidovorans* and *Pseudomonas aeruginosa*. The alkane can increase the amount of heterotrophic bacteria in the location adjacent to the plant, and thereby accelerate a heterotrophic nitrification process. The butane substrate can also stimulate the growth of butane-utilizing fungi. The method can also enhance the growth protists and/or prokaryotes. A system for enhancing plant growth in accordance with the method is also disclosed.

Alkane enrichment, preferably butane, increases the indigenous microbial populations in soil within the region of plant growth—the rhizosphere. This increase in microbial populations may provide direct benefits such as increased nutrient uptake, faster root development, and reduced heat, drought and cold stress, as well as accelerated root development and stimulation of plant growth.

BRIEF DESCRIPTION OF THE DRAWINGS

FIG. 3 is a schematic representation of enhanced plant growth in a vessel including a butane injector in comparison with a vessel without a butane injector.

FIG. 5 includes comparative pictorial representation s showing plant root growth in a butane enhanced vessel versus root growth in a control vessel.

DETAILED DESCRIPTION OF THE INVENTION

It is known that the addition of beneficial microorganisms to a soil mix, growing bed or crop may help prevent disease and increase plants' nutrient uptake, growth and development, and tolerance to stresses such as cold, heat and drought. Currently, many commercial growers use microbial enhancement/inoculation products that are available in the form of powder or concentrated liquid that is mixed with water, or in a granular form that is mixed into soil. Some products are mixed with nutrients that also increase the number of existing bacteria.

Plant roots provide suitable habitats for the growth of microorganisms, and particularly high numbers of many different microbial populations are found on and surrounding plant roots (rhizosphere). Interactions between soil microorganisms and plant roots satisfy important nutritional requirements for both the plant and the associated microorganisms.

Microbial populations in the rhizosphere may benefit plants in a variety of ways, including increased recycling and solubilization of mineral nutrients; synthesis of vitamins, amino acids, auxins and gibberellins, which stimulate plant growth; and antagonism with potential plant pathogens through competition and development of amensal relationships (detrimental to one while not adversely affecting the other) based on the production of antibiotics.

The present invention provides biostimulation of plant growth through alkane injection into soil or other growth media. The alkane may include methane, ethane, propane and/or butane, with butane being preferred. In one embodiment of the invention, butane may be injected in crop fields using underground injection piping. For example, farms which currently employ underground injection methods for ammonia and fertilizer applications may be modified to inject butane into the root zone of crops using the network distribution piping. The immediate environment of plant root surfaces is referred to as the rhizoshere. When aerobic biostimulation is desired, such injection piping may also be supplied with an oxygen-containing gas such as air. Thus, butane injection systems of the present invention may be newly installed in crop fields or retrofitted into crop fields with existing underground piping.

Figure 1:
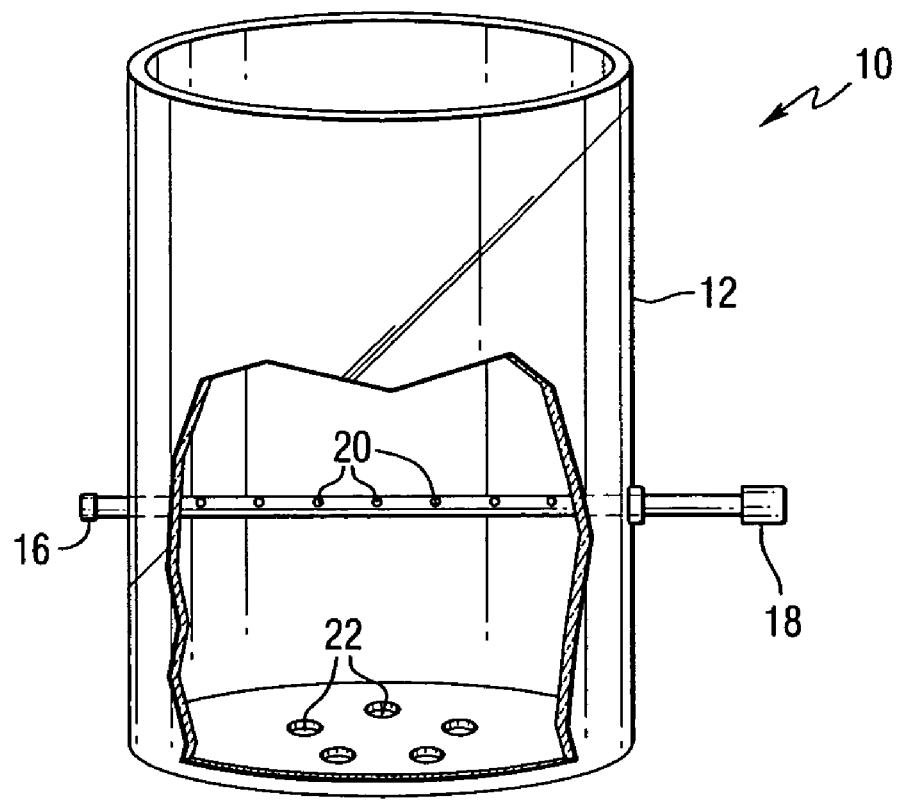
FIG. 1 is a schematic representation of a plant growth vessel including a perforated butane injection tube in accordance with an embodiment of the present invention.

Referring to the drawings, FIG. 1 is a schematic representation of a plant growth vessel 10 including cylindrical container 12 constructed in accordance with an embodiment of the present invention. The container can be a Nalgene plastic container. A perforated butane injection tube 14 is positioned in the container and can pass through the container and can be sealed at one end, for example by a plug 16. The other end of the injection tube can include a syringe port 18 equipped with Teflon-coated septum for butane injections. A plurality of holes 20 are provided in the tube for the delivery of butane to the root zone of plants in the vessel. Drainage holes 22 can provided in the bottom of the vessel.

Figure 2:
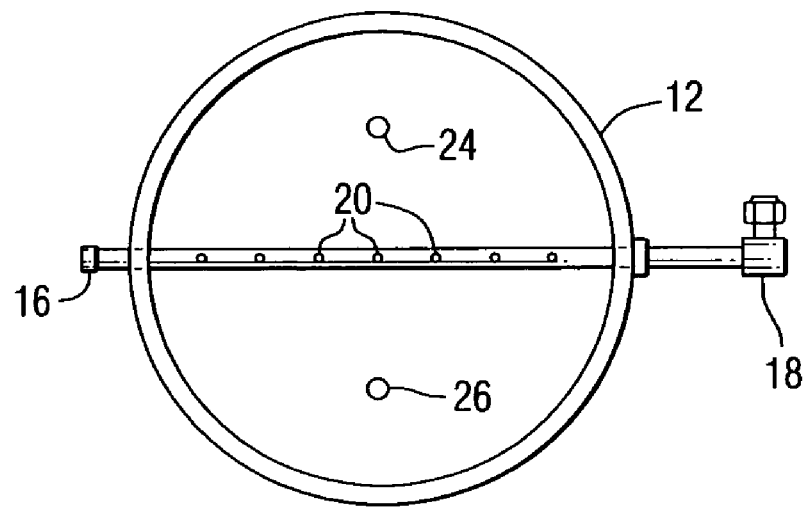
FIG. 2 is a top view of the vessel of FIG. 1.

FIG. 2 is a top view of the vessel of FIG. 1. Seed positions 24 and 26 show the approximate locations of seeds used in the examples discussed below.

FIG. 3 is a schematic representation of a control vessel and an enhanced plant growth vessel, and illustrates enhanced plant growth produced by this invention. The control vessel 28 contains two seedlings 30, 32, that have been grown without the benefit of alkane injection. The enhanced plant growth vessel 10 contains two seedlings 34, 36 that were grown with the benefit of alkane injection. The control vessel and the enhanced plant growth vessel include soil 38 and 40 respectively, as well as gravel 42 and 44 for drainage.

In accordance with an embodiment of the present invention, injecting butane into the root zone of plants as a food source encourages the naturally occurring bacteria already acclimated to site conditions to flourish. Although not intending to be bound by any particular theory, butane injection may provide several benefits, as described in detail below.

Soil organic matter (SOM) is an accumulation of dead plant matter, partially decayed and partially resynthesized plant and animal residues, and live microbial and root matter. SOM contributes to plant growth through its effects on the chemical, biological and physical properties of soil. SOM supplies nitrogen, phosphorus and sulfur for plant growth, serves as an energy source for soil microfloral and macrofaunal organisms, and promotes good soil structure. SOM content is directly related to the sorption of most herbicides and many organic compounds. Organic chemicals associate with the organic fraction of soils. Thus SOM content strongly influences pesticide behavior in soil, including effectiveness against target species, phytotoxity to subsequent crops, leachability, volatility and biodegradability. Injecting butane in the root zone may increase SOM.

Humus is the organic portion of the soil remaining after microbial decomposition. Humus is a complex and rather microbially resistant mixture of brown to black, amorphous and colloidal substances modified from the original plant tissues or resynthesized by soil microorganisms. Humus affects soil structure. Aeration, water holding capacity and permeability are all favorably affected by humus. Butane injection will lead to an increase in soil microorganisms, which will lead to an increase in soil humus content.

Increases in bacteria may result in an increase in enzymes, nutrients and biochemical reactions/interactions with soil organic material (SOM) and humus that lead to the formation of additional compounds that are beneficial to plants. Butane enhancement and the resulting increase in bacteria may also lead to improvement in soil properties such as soil structure, aeration, water holding capacity and permeability, as well as the improved performance of herbicides, fungicides, pesticides and other agricultural chemicals.

The increases in soil bacteria and cell respiration due to butane injection may lead to increased amounts of carbon dioxide available to plants, which is used directly by plants during photosynthesis. Furthermore, butane injected into the root zone may also provide a direct benefit as a nutrient to plants.

Increased root growth due to butane injection may enable plants to reach groundwater at greater depths and thus enable plants to thrive under more harsh conditions, and in areas/climates where plants have not previously been able to thrive, or in less than optimal soil conditions.

Increased plant growth/plant size due to butane injection may lead to increased quantities of fruit, flowers, vegetables, legumes or grains produced by individual plants, or to increased size of individual fruit, flowers, ornamental flowers, vegetables, legumes or grains produced by plants.

Increased rate of seed germination due to butane injection may lead to increased numbers of plants produced by an individual seeding/planting event.

Increased plant ability to resist pests, diseases, lethal bacteria and fungi due to butane injection may lead to an increased survival rate of plants that will result in increased production of plants, fruit, flowers, vegetables, legumes or grains during a growing season.

Increased rate of plant growth due to butane injection may lead to an increased number of possible cycles of individual seedings/planting events followed by growth period and harvesting events within an individual growing season, with the possibility of producing the outcome of two growing seasons in one.

Increased plant ability to endure stress, such as cold, heat or drought due to butane injection may lead to a longer growing season.

Increased plant size or number of plants due to butane injection into the root zone may lead to increased production of oxygen in the atmosphere resulting from the process of photosynthesis.

Butane may be injected, for example, through existing piping networks that deliver nutrients and agricultural chemicals to the soil subsurface. Butane may be injected alone, simultaneously or intermittently with other nutrients or chemicals. Butane may also be injected simultaneously or intermittently with air or other gases.

Butane may be injected into all soil types, including soilless mixtures used for growing plants. Butane may be injected into the root zone of plants grown outdoors or in greenhouses. Butane may be injected into hydroponic and aeroponic growing systems, which use no soil. Butane may be injected into aquatic growing systems, such as seaweed or kelp beds, and semi-aquatic growing systems or fields, such as puddled rice fields or paddies.

The present method of butane enhanced plant growth may be applied to all plants, grasses, trees, shrubs, vines, fruit, flowers, legumes, grains and mosses in the Kingdom Plantae, for example, flowering monocot and dicot plants (phyla Angiospernophyta, class Monocotyledoneae, class Dicotylodoneae,); conifers (phyla Ginkgophyta, Gnetophyta, Cycadophyta and Coniferophyta); non vascular plants including mosses (phylum Bryophyta), liverworts (phylum Hepatophyta), hornworts (phylum Anthoceraphyta); and ferns (phyla Filicinophyta, Sphenophyta, Lycodophyta and Psilophyta).

Many plants are dependent on the help of fungi to get nutrients, and live in a symbiotic relationship with fungi called mycorrhizal association. They obtain food by absorbing dissolved inorganic and organic materials. They digest food outside their bodies. Typically a fungus will secret digestive enzymes onto a food source and absorb the smaller molecules released. Mycorrhizal associates (plants) benefit from this by absorbing materials digested by the fungi growing among their roots.

Enhanced uptake of water and mineral nutrients, particularly phosphorus and nitrogen, has been noted in many mycorrhizal associations. Plants with mycorrhizal fungi are therefore able to occupy habitats they otherwise could not. The importance of mycorrhizal association was first recognized in connection with efforts to grow orchids in greenhouses. Orchids have microscopic seeds that germinate to form a tiny pad of tissue called a protocorm. Cultivaters of orchids found that the plants seldom developed beyond the protocorm stage unless they were infected by a particular kind of fungus. It has also been found that if seedlings of forest trees are grown in nutrient solutions and then transplanted to prairie and other grassland soils they fail to grow. Eventually they die from malnutrition despite the fact that soil analysis shows that here are abundant nutrients in the soil. If a small amount of forest soil containing fungi is added around the roots of the seedlings, however, they will grow promptly and normally. The fungus may form a sheath around the root. The role of water and mineral uptake of the root is partially assumed by the fungi. Butane injection leads to an increase in SOM, and therefore an increased food source for fungi, which provide benefits for increased plant growth. Increased plant growth may indicate that butane injection in the root zone may be used directly as a nutrient by fungi, or may stimulate conditions that lead to improved growth of fungi and improved performance during mycorrhizal association.

Protists have characteristics of plants, fungi and animals. Protists inhabit many different environments—fresh water, seawater, soils and the intestinal tracts of animals, where they perform crucial digestive processes. The protists include such organisms as algae, seaweed, amoebas and slime molds. Like plants, many species of protists can make their own food by the process of photosynthesis. The photosynthetic protists are the green algae (Chlorophyta), brown algae (Phaephyta) that include seaweed and kelp, red algae (Rhodophyta), Bacillariophyta and Dinophyta. Algae are extremely important as a source of food for other aquatic organisms and also make a major contribution to the world's oxygen supply.

Green algae are also found in damp soil, attached to land plants (a few are parasitic), and even in snow and ice. The marine forms are often visible on coastal rocks exposed at low tide. Some terrestrial species combine with fungi in symbiotic associations called lichens.

Some red algae are also important in the formation of tropical reefs, an activity with which they have been involved for millions of years. In some Pacific atolls, red algae have contributed far more to reef structure than other organisms, even more than corals. These reef-building rhodophytes are called coralline algae, because they secrete a hard shell of carbonate around themselves, in much the same way that corals do.

Coral reefs are widely recognized as highly productive, ecologically valuable, and economically important ecosystems that, because of their particular sensitivity to environmental changes, are experiencing a world-wide decline.

Butane injection increases numbers of indigenous bacteria in soil and water. These bacteria produce carbon dioxide during respiration. Some protists use carbon dioxide as a food source during photosynthesis. Increased availability of carbon dioxide may lead to increased numbers of protists or increased size of protists, or increased ability of protists to thrive under conditions of stress, in climates or environments where protists do not usually thrive. Butane injection may be used directly as a nutrient by protists, or may stimulate conditions that lead to improved growth of protists.

Prokaryotes include bacteria and archaebacteria. They are responsible for the decay and recycling of organic material in soil. Their activities release nutrients and make them available to plants. Some prokaryotes perform nitrogen fixation, and some prokaryotes are photosynthetic, such as blue-green algae (cyanobacteria). Blue green algae are found in soil, on rocks, in salt water and freshwater. They use carbon dioxide as a food source during photosynthesis. Some blue green algae are capable of nitrogen fixation. In Southeast Asia, rice can be grown on the same land for years without the addition of fertilizers because of the rich growth of nitrogen-fixing blue-green algae in the rice paddies. Blue green algae are nutritionally independent (require only $N_2$ and $CO_2$-atmosphere suffices) and are able to colonize on areas of bare rock and soil. Blue green algae formed a gelatinous growth on pumice and volcanic ash within a few years of a cataclysmic volcanic explosion on the island of Krakatoa in Indonesia in 1883. The growth was thick enough to serve as a substrate for the growth of higher plants. Butane injection may lead to an increase in SOM, which is a food source for some prokaryotes, thereby increasing the number of prokaryotes. Butane injection may also lead to an increase in bacteria, which produce carbon dioxide during respiration. Increases in carbon dioxide available to photosynthetic prokaryotes will lead to an increase in numbers of prokaryotes in a growth substrate.

Bacteria utilized in accordance with the biostimulation methods of the present invention may include the following Groups (in addition to fungi, algae, protozoa, rotifers and other aerobic and anaerobic microbial populations found in decaying materials):

Group 1: The Spirochetes

Group 2: Aerobic/Microaerophilic, motile, helical/vibroid, gram-negative bacteria Group 3: Nonmotile (or rarely motile), gram-negative bacteria Group 4: Gram-negative aerobic/microaerophilic rods and cocci Group 5: Facultatively anaerobic gram-negative rods Group 6: Gram-negative, anaerobic, straight, curved, and helical bacteria
Group 7: Dissimilatory sulfate- or sulfur-reducing bacteria
Group 8: Anaerobic gram-negative cocci
Group 9: Anoxygenic phototrophic bacteria
Group 10: Oxygenic phototrophic bacteria
Group 11: Aerobic chemolithotrophic bacteria and associated organisms
Group 12: Budding and/or appendaged bacteria
Group 13: Sheathed bacteria
Group 14: Nonphotosynthetic, nonfruiting gliding bacteria
Group 15: The fruiting, gliding bacteria and the Myxobacteria
Group 16: Gram-positive cocci
Group 17: Endospore-forming gram-positive rods and cocci
Group 18: Regular, nonsporing, gram-positive rods
Group 19: Irregular, nonsporing, gram-positive rods
Group 20: The mycobacteria
Groups 21-28: The actinomycetes
Group 21: Nocardioform actinomycetes
Group 22: Genera with multiocular sporangia
Group 23: Actinoplanetes
Group 24: Streptomycetes and related genera
Group 25: Maduromycetes
Group 26: Thermomonospora and related genera
Group 27: Thermoactinomycetes
Group 28: Genus Glycomyces, Genus Kitasatospira and Genus Saccharothrix
Group 29: The Mycoplasmas—cell wall-less bacteria
Group 30: The Methanogens
Group 31: Archacal sulfate reducers
Group 32: Extremely halophilic, archaeobacteria (halobacteria)
Group 33: Cell wall-less archaeobacteria
Group 34: Extremely thermophilic and hyperthermophilic $S^0$-metabolizers In addition to the above-listed bacteria examples, facultative anaerobes and microaerophilics, which are bacteria capable of surviving at low levels of oxygen, may also be used in accordance with the present invention. They do not require strict anaerobic conditions such as the obligate anaerobes. Examples include acidophilic, alkaliphilic, anaerobe, anoxygenic, autotrophic, chemolithotrophic, chemoorganotroph, chemotroph, halophilic, methanogenic, neutrophilic, phototroph, saprophytic, thermoacidophilic and thermophilic bacteria.

EXAMPLE 1

On Day No. 1, two Nalgene plastic vessels (one for butane enhanced growth and one for control) approximately 11 cm in diameter and 6.5 cm deep were prepared with 0.4 cm drainage holes drilled in each base. The butane enhanced growth vessel (illustrated in FIG. 1) was prepared with a 12 cm section of Teflon tubing sealed outside the vessel at one end and connected at the other end to a syringe port equipped with Teflon-coated septum for butane injections. The tubing intersected the vessel through the diameter at a height of 1.5 cm above the base. Nine butane injection holes were placed at 1 cm intervals along the tubing inside the vessel. Each vessel was filled with approximately 523 cm³ of Iowa Crop Soil (soil depth=5.5 cm) that had been collected from an Iowa commercial cornfield. The soil in each vessel was tested for pH using a Chemetrics pH meter dipped in a mixture of 40 ml distilled water and 100 grams of soil. Soil tests returned pH of 7.2 in both vessels.

Each vessel was seeded with two seeds of sweet corn, variety Sugar Dots, placed (illustrated in FIG. 2) at a depth of 2.54 cm below soil surface. Each vessel was then watered with 100 ml spring water and positioned on its own drainage tray on a shelf approximately 10 cm below two 33 watt grow light tubes (no sunlight) equipped with a timer set for 16 hours light on, 6 hours light off. White reflective covering was placed on the wall immediately behind the samples, with an aluminum foil hood extending over the light fixture to reflect light downward onto the vessels.

Ambient temperature was recorded, water was sprinkled evenly over the soil surface of each vessel, and n-butane was injected into the root zone (rhizosphere) through the syringe port of the butane enhanced growth vessel according to the regimen in Table 1.

TABLE 1

Butane Injection Schedule

| Day No. | Time | Volume of Butane | Water added | Ambient Temperature |
|---|---|---|---|---|
| 1 | 13:30 | 50 ml | 100 ml | 76° |
| 2 | 10:47 | 50 ml | N/A | 74° |
| 2 | 13:30 | 50 ml | N/A | 74° |
| 5 | 16:30 | 100 ml | 50 ml | 76° |
| 6 | 12:30 | 100 ml | 50 ml | 78° |
| 7 | 13:15 | 50 ml | N/A | 76° |
| 7* | 18:00 | 100 ml | 50 ml | 76° |
| 8 | 13:00 | 100 ml | N/A | 76° |
| 8 | 18:00 | 100 ml | N/A | 76° |
| 9 | 10:30 | 100 ml | N/A | 76° |

Figure 4:
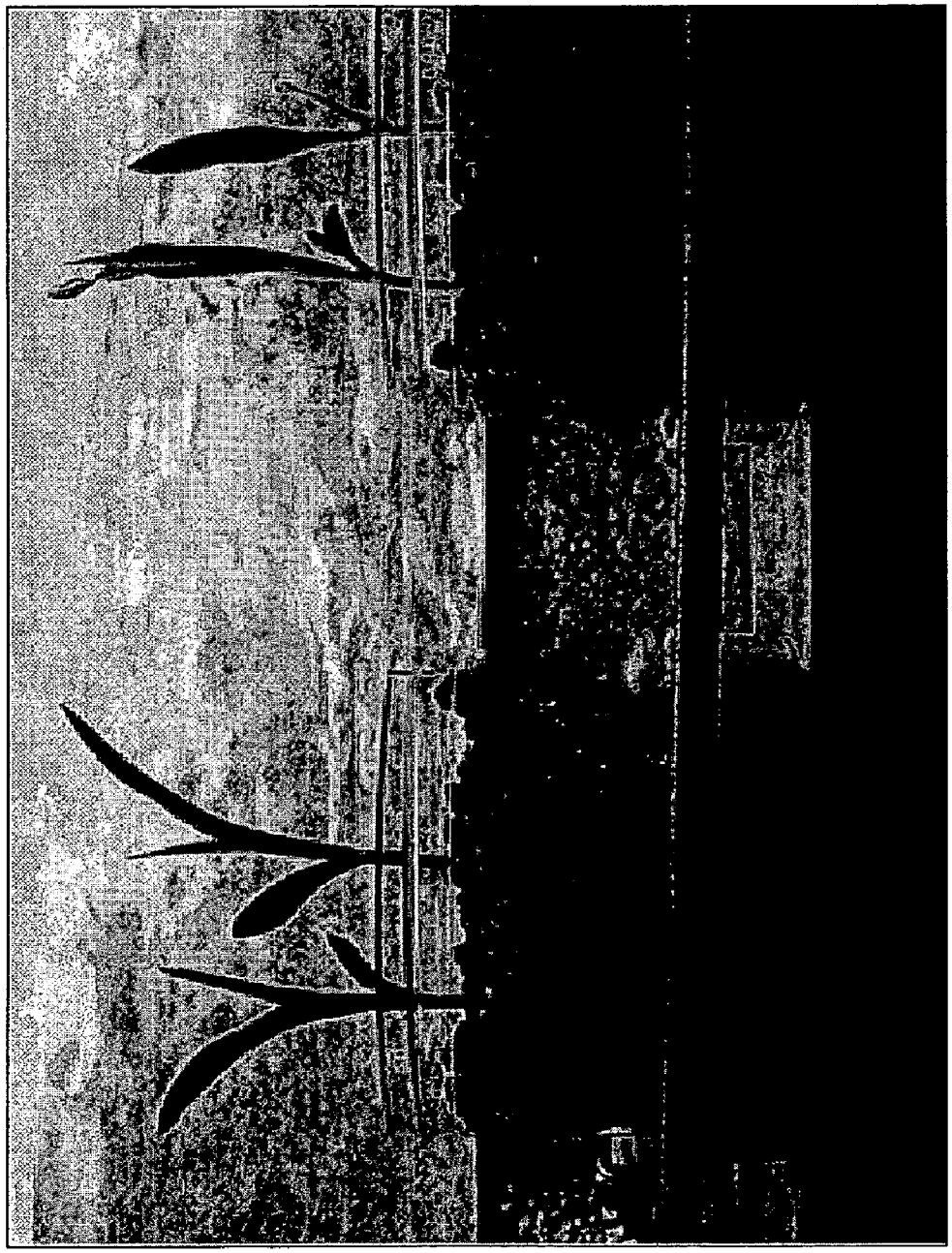
FIG. 4 is a pictorial representation of seedlings grown with butane enhancement in comparison with a control sample in which seedlings were grown without butane enhancement.

Seedling height for the last four days of growth is recorded in Table 2. FIG. 4 is a pictorial representation of the butane enhanced and control seedlings of Example 1.

TABLE 2

Seedling Height

| Sweet Corn Sugar Dots Day No. | Butane Enhanced Growth | Control |
|---|---|---|
| 1 | — | — |
| 2 | — | — |
| 3 | — | — |
| 4 | — | — |
| 5 | — | — |
| 6 | 0.5 cm, 0.8 cm | 0.5 cm, 1.0 cm |
| 7 | 4.0 cm, 4.5 cm | 5.0 cm, 5.5 cm |
| 8 | 7.0 cm, 6.0 cm | 6.8 cm, 6.5 cm |
| 9 | 11.0 cm, 6.8 cm | 8.8 cm, 9.8 cm |

Figure 6:
FIG. 6 is a pictorial representation comparing root lengths for plants grown with butane enhancement versus root lengths for plants grown without such enhancement.

On Day No. 9, all four plants (two butane enhanced growth and two control) were unearthed to the extent possible without damaging the root system to reveal the root ball (roots and soil clinging to roots) and longest roots of each plant. FIG. 6 is a pictorial representation of the unearthed plants of Example 1.

On the last four days of growth, water droplets were observed clinging to the leaves of the butane-enhanced plants.

The root systems of the butane enhanced and control plants were visible through the sides of the clear grow vessels, as shown in the pictorial representation of FIG. 5. The roots of the butane-enhanced plants were observed to spread to a greater and more complex degree horizontally than the roots of the control plants. Unearthing of the four plants revealed that the two butane-enhanced plants had longer roots (25 cm and 12 cm) and larger roots ball than the two control plants (11 cm and 8 cm). The root branches of the butane enhanced plants also appeared to be longer and greater in number than the root branches of the control plants. The thickness and color (grayish white) of the roots appeared to be the same in the butane-enhanced and control plants.

The butane-enhanced plants each grew to a maximum of 11 cm and 6.8 cm in height. The control plants reached heights of 8.8 cm and 9.8 cm on the final day of growth.

EXAMPLE 2

On Day No. 1, two Nalgene vessels, (one for butane enhanced growth and one for control) approximately 11 cm in diameter and 13 cm deep, were prepared with five 0.4 cm drainage holes drilled in each base. The butane enhanced growth vessel (illustrated in FIG. 1) was prepared with a 12 cm section of Teflon tubing sealed outside the vessel at one end and connected at the other end to a syringe port equipped with Teflon-coated septum for butane injections. The tubing intersected the vessel through the diameter at a height of 3.5 cm above the base. Nine butane injection holes were placed at 1 cm intervals along the tubing inside the vessel. Each vessel was filled with approximately 902 cm$^3$ of Iowa Crop Soil (soil depth=9.5 cm) that had been collected from an Iowa commercial cornfield. The soil in each vessel was tested for pH using a Chemetrics pH meter dipped in a mixture of 40 ml distilled water and 100 grams of soil. Soil tests returned pH of 7.2 in both vessels.

Each vessel was seeded with two seeds of sweet corn, variety Sugar Dots, (using the seed positions shown in FIG. 2) placed at a depth of 2.54 cm below soil surface. Each vessel was then watered with 100 ml spring water and positioned on its own drainage tray on a shelf approximately 10 cm below three 33 watt grow light tubes (no sunlight) equipped with a timer set for 16 hours light on, 6 hours light off. White reflective covering was placed on the wall immediately behind the samples, with an aluminum foil hood extending over the light fixture to reflect light downward onto the vessels.

Ambient temperature was recorded, water was sprinkled evenly over the soil surface of each vessel, and n-butane was injected into the root zone through the syringe port of the butane enhanced growth vessel according to the regimen in Table 3.

TABLE 3

Butane Injection Schedule

| Day No. | Time | Volume of Butane | Water added | Ambient Temperature |
|---|---|---|---|---|
| 1 | 13:00 | 100 ml | 100 ml | 78° |
| 1 | 18:00 | 100 ml | N/A | 78° |
| 2 | 08:00 | 100 ml | N/A | 74° |
| 2 | 13:00 | 100 ml | N/A | 76° |
| 2 | 09:26 | 100 ml | 50 ml | 74° |
| 3 | 14:00 | 100 ml | N/A | 76° |
| 3* | 18:25 | 100 ml | N/A | 76° |
| 4 | 08:35 | 100 ml | N/A | 74° |
| 4 | 13:30 | 100 ml | N/A | 76° |
| 4 | 18:30 | 100 ml | N/A | 76° |
| 5 | 15:50 | 100 ml | N/A | 74° |
| 5 | 17:45 | 50 ml | N/A | 74° |
| 6 | 19:10 | 100 ml | 40 ml | 72° |
| 6 | 20:35 | 50 ml | N/A | 74° |
| 7 | 08:10 | 100 ml | N/A | 68° |
| 7 | 13:00 | 100 ml | N/A | 72° |
| 7 | 18:30 | 100 ml | N/A | 72° |
| 8 | 09:00 | 100 ml | N/A | 74° |
| 8 | 16:15 | 100 ml | N/A | 76° |
| 8 | 20:00 | 100 ml | 50 ml | 76° |
| 9 | 09:20 | 100 ml | N/A | 76° |
| 9 | 13:30 | 100 ml | N/A | 76° |
| 9 | 18:30 | 100 ml | N/A | 76° |
| 10 | 07:30 | 100 ml | N/A | 74° |
| 10 | 12:30 | 100 ml | N/A | 74° |
| 10 | 18:30 | 100 ml | N/A | 74° |
| 11 | 09:30 | 100 ml | N/A | 74° |
| 11 | 12:45 | 100 ml | N/A | 82° |
| 11 | 20:00 | 100 ml | 50 ml | 82° |
| 12 | 09:35 | 100 ml | N/A | 74° |
| 12 | 13:00 | 100 ml | N/A | 74° |
| 12 | 18:00 | 100 ml | N/A | 74° |
| 13 | 18:20 | 150 ml | N/A | 68° |
| 14 | 07:50 | 100 ml | N/A | 58° |
| 14 | 11:30 | 100 ml | N/A | 68° |
| 14 | 18:30 | 100 ml | N/A | 68° |
| 15 | 07:30 | 100 ml | N/A | 57° |
| 15 | 13:30 | 100 ml | N/A | 68° |
| 15 | 19:30 | 100 ml | 50 ml | 68° |
| 16 | 07:30 | 100 ml | N/A | 60° |
| 16 | 13:00 | 100 ml | N/A | 64° |
| 16 | 19:00 | 100 ml | N/A | 68° |

Figure 7:
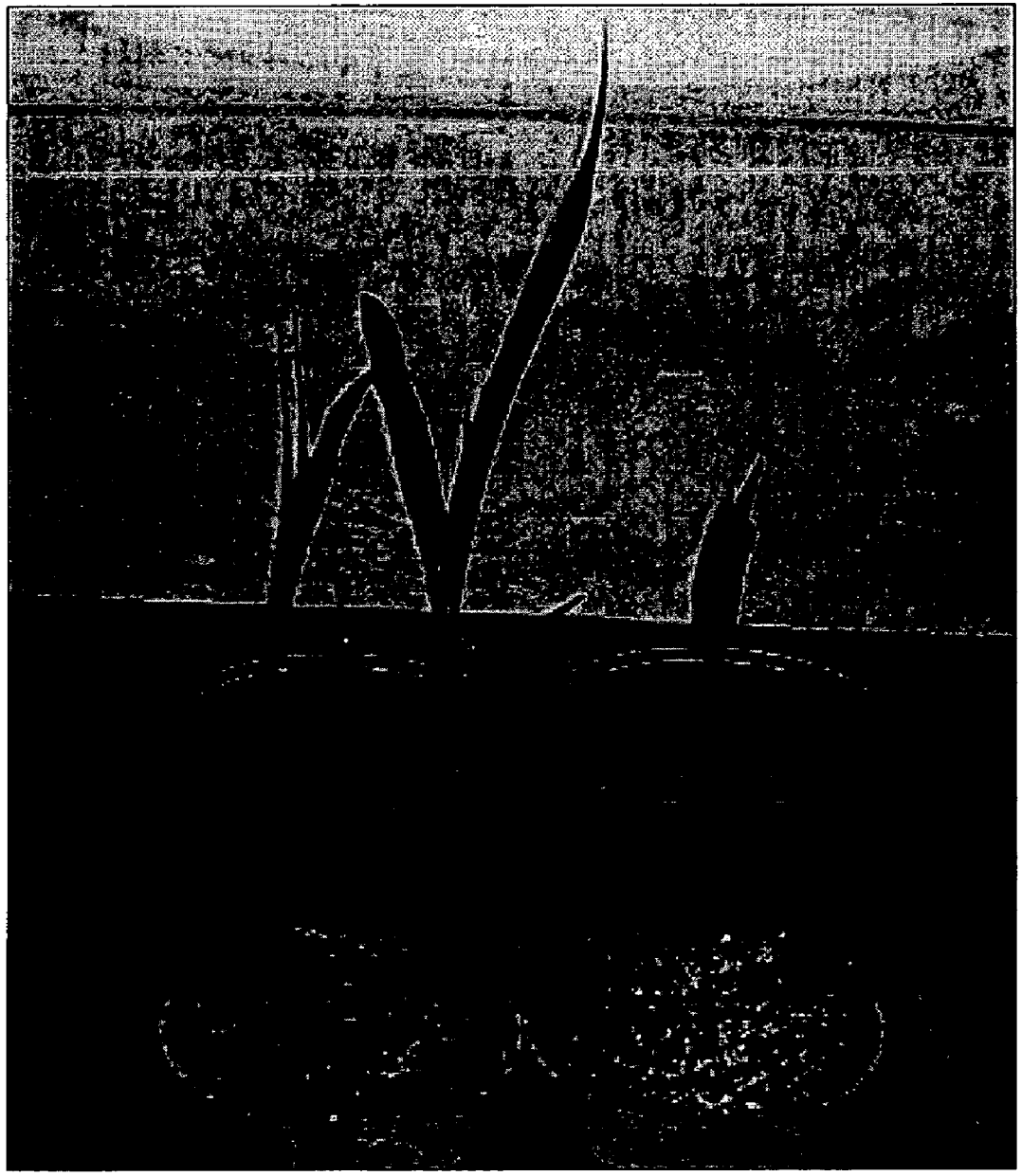
FIG. 7 is a pictorial representation comparing seedlings growth in a vessel with butane enhancement versus seedlings grown in a vessel without butane enhancement.

Plant growth as observed for sixteen days. Seedling height is recorded in Table 4. FIG. 7 is a pictorial representation showing the seedlings of Example 2.

TABLE 4

Seedling Height

| Sweet Corn Sugar Dots Day No. | Butane Enhanced Growth | Control (Only 1 seed sprouted) |
|---|---|---|
| 1 | — | — |
| 2 | — | — |
| 3 | — | — |
| 4 | — | — |
| 5 | 0.5 cm, 1.0 cm | — |
| 6 | 3.0 cm, 3.0 cm | — |
| 7 | 4.0 cm, 4.0 cm | — |
| 8 | 6.0 cm, 5.7 cm | 0.8 cm |
| 9 | 8.0 cm, 7.2 cm | 2.7 cm |
| 10 | 11.0 cm, 9.1 cm | 4.0 cm |
| 11 | 16.0 cm, 12 cm | 6.5 cm |
| 12 | 18.0 cm, 15.5 cm | 8.2 cm |
| 13 | 19.0 cm, 16.7 cm | 8.9 cm |
| 14 | 20.1 cm, 17.3 cm | 9.6 cm |
| 15 | 22.0 cm, 18.0 cm | 11.0 cm |
| 16 | 27.0 cm, 19.6 cm | 15.0 cm |

Figure 11:
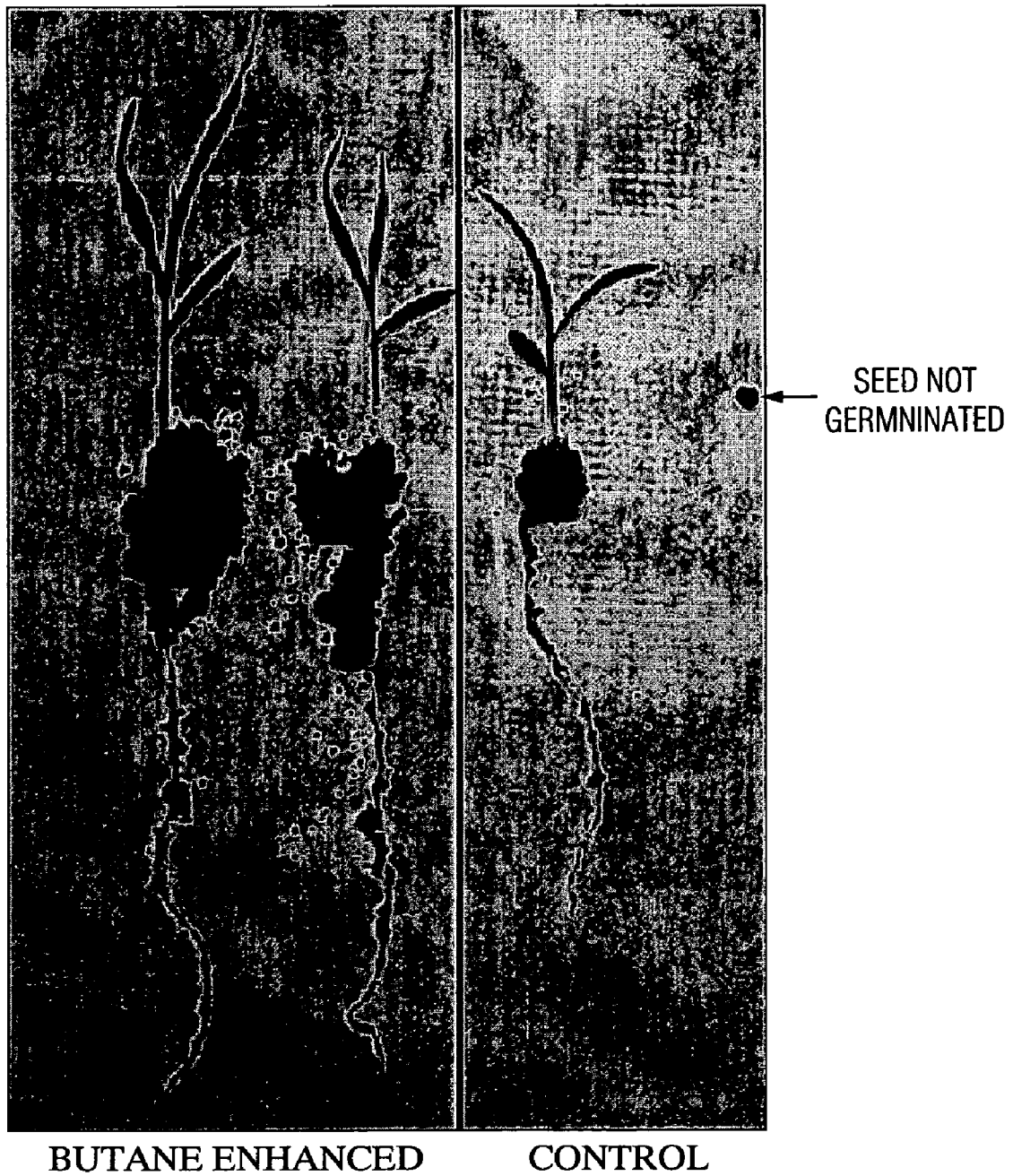
FIG. 11 is a pictorial representation comparing butane enhanced root growth versus non-butane enhanced root growth.
Figure 12:
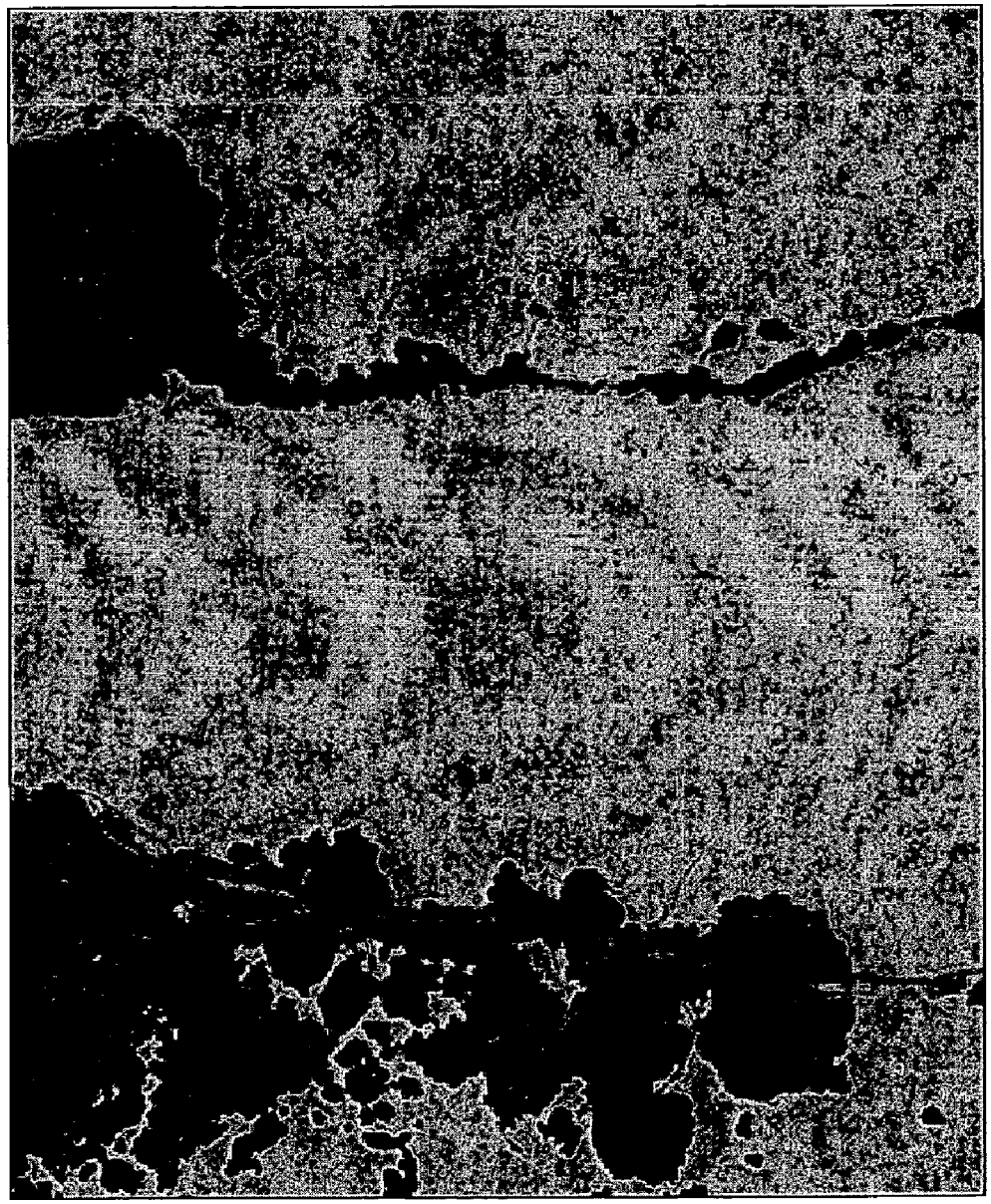
FIG. 12 is a pictorial representation comparing butane enhanced root growth versus non-butane enhanced root growth.

On Day No. 16, all three corn plants (two butane enhanced growth and one control) were unearthed to the extent possible without damaging the root system to reveal the root ball (roots and soil clinging to roots) and longest roots of each plant. FIGS. 11 and 12 show the unearthed seedling of Example 2.

The two corn seeds planted in the butane enhanced growth vessel sprouted into seedling, while only one of the seeds planted in the control vessel (no butane) sprouted. One seed in the control vessel never germinated, with the seed coat observed to be still firm and unbroken when unearthed on Day No. 16. The butane enhanced plants sprouted three days earlier than the control plant.

Soil moisture content in the butane enhanced growth and control vessels remained high throughout the experiment. All plants received the same amount of water. The significant increase in growth rate and size of the butane enhanced plants over the one sprouted control plant did not appear to result in an increase in the rate of "drying out" of the soil, perhaps indicating that butane enhancement increases soil capacity to hold water.

The leaves of the butane enhanced corn plants and the control corn plant exhibited the same color (medium green) and shape, while the stems of all plants were light green with a purplish tint near the base of the stem. On the last day of growth the stems of the butane enhanced plants were 0.5 cm (taller plant) and 0.3 cm (shorter plant) in thickness. The stem of the control plant was 0.25 cm in thickness.

The control corn plant grew at an average rate of 0.94 cm per day over the sixteen-day period, while the butane enhanced corn plants grew at an average rate of 1.45 cm per day. The butane enhanced plants exhibited a 54% faster growth rate than the control plant. The control plant achieved growth in height of 15.0 cm, while the butane enhanced plants achieved an average growth in height of 23.3 cm. The butane enhanced corn plants grew to an average height 55% taller than the control corn plant.

Figure 8:
FIG. 8 is a pictorial representation showing butane enhanced root growth.
Figure 9:
FIG. 9 is a pictorial representation showing root growth in a control sample without butane enhancement.
Figure 10:
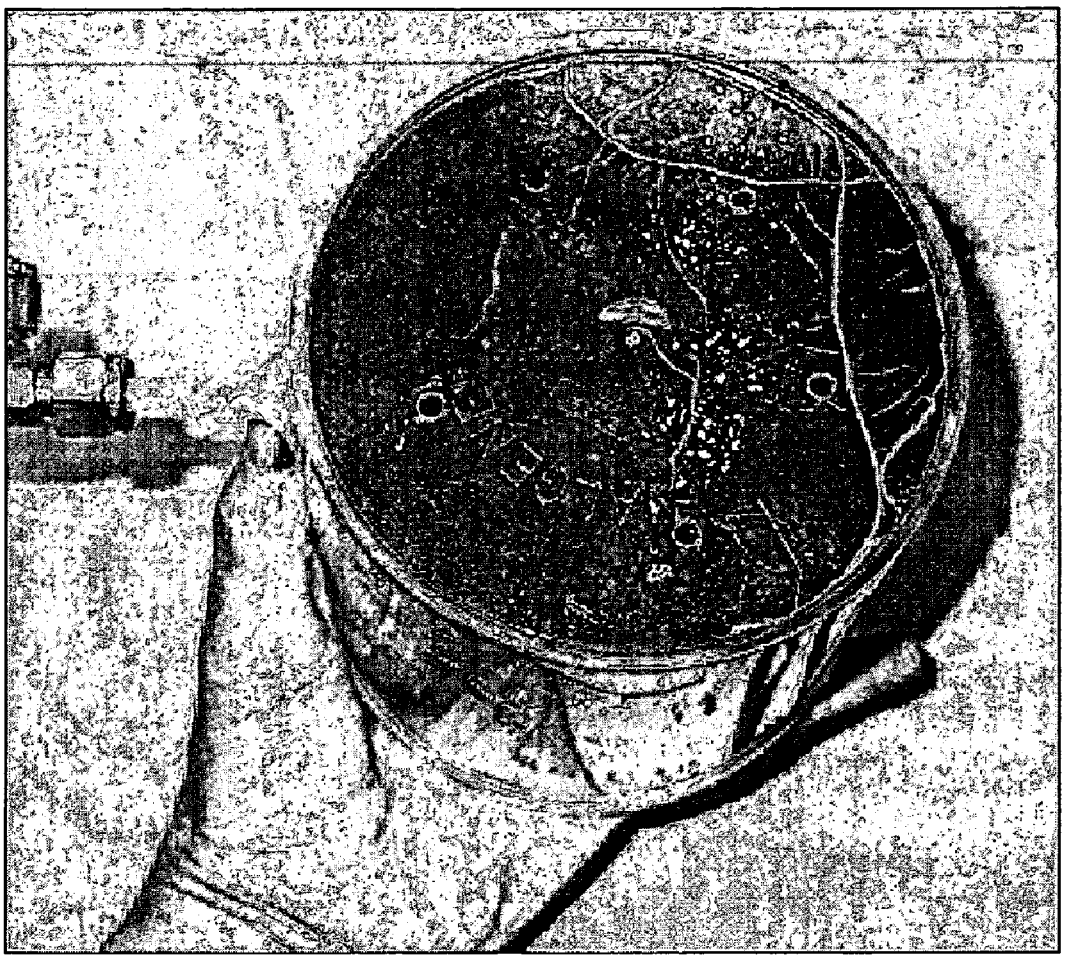
FIG. 10 is a pictorial representation showing butane enhanced root growth at the bottom of a vessel.

Roots of the butane enhanced plants and the control plant were visible through the clear vessels. The main root of the control plant was observed to have tiny root branches shorter than 0.25 cm (as shown in FIG. 9). The main roots of the butane enhanced plants were observed to be of the same thickness as that of the control plant. However, the root branches of the butane enhanced plants were observed to be longer, up to 3 cm in length (as shown in FIGS. 8 and 10).

After the plants were unearthed and soil was removed to the extent possible without damaging the roots, the main (longest) roots of all plants were compared and measured (approximately due to presence of remaining soil). FIG. 12 shows the unearthed plants of Example 2. The main roots of the butane enhanced plants were longer than the control plant main root. The main root of the taller (27 cm) butane enhanced plant was approximately 30 cm in length, while that of the shorter (19.6 cm) butane enhanced plant was approximately 25 cm long. The main root of the control plant was approximately 20 cm long. Again, the root branches of the butane enhanced plants were longer and greater in number than those of the control plant (as shown in FIG. 11).

In both Examples 1 and 2, butane injection is associated with growth of longer and more complex root systems in sweet corn plants, variety Sugar Dots. In both Examples 1 and 2, water droplets were observed on several days following watering events. This "sweating" activity of the plant is probably due to absorption of excess water by the expanding root system resulting from butane treatment.

Although the results achieved in Example 1 were inconclusive regarding the advantage in height of butane enhanced plants over the control plants, the outcome of Example 2, in which increased amounts of butane were injected into the root zone, clearly showed the butane enhanced plants significantly surpassed the control plant in average growth rate and average growth in height.

The method and apparatus of this invention can be applied to agricultural crops, as well as other plants, protists and/or prokaryotes. For aerobic treatment, an oxygen-containing gas may also be introduced into the organic matter. The introduction of oxygen-containing gas may be accomplished by any suitable means such as injection tubes for introducing the gas alone or in a carrier fluid, or by exposing the material to the atmosphere. In one embodiment of the invention, the alkane is butane, but other compounds can be used such as methane, ethane, propane or any higher order alkane.

The alkane can be supplied from an alkane source such as alkane cylinder and can be delivered to locations adjacent to plants, protists and/or prokaryotes using one or more injectors, with an end or other portion of the injectors extending into the desired location. The alkane source can be connected to the injectors through one or more pipes or tubes. The alkane can be injected with a pusher gas, such as helium. One or more valves can be used between the alkane source, a pusher gas source, and the injectors to control the flow of the alkane and the pusher gas. A controller can be provided to control the valve, and the controller can include a timer that controls the timing of operation of the valve. The alkane can be supplied in gaseous or liquid form. Various forms of injectors can be used, including injectors having a proximal for receiving the alkane and a distal end for dispersing the alkane. The distal end can include a plurality of openings.

As used herein, the term "butane substrate" includes liquids and gases in which butane is present in sufficient amounts to stimulate substantial growth of butane-utilizing bacteria. Butane is preferably the most prevalent compound of the butane substrate on a weight percent basis, and typically comprises at least about 10 weight percent of the butane substrate. The other constituents of the butane substrate may include other hydrocarbon compounds, such as other alkanes, i.e., methane, ethane and propane. The butane substrate preferably comprises at least about 50 weight percent butane. More preferably, the butane substrate comprises at least about 90 weight percent butane. In a particular embodiment, the butane substrate comprises at least about 99 weight percent n-butane. The butane may contain straight (n-butane) and/or branched chain compounds such as iso-butane.

Butane is highly soluble and ideally suited to serve as a microbial growth substrate, thereby significantly increasing the heterogeneous microbial community. The enhanced microbial population will rapidly absorb and mineralize the degradable and available dissolved organic nutrients in the organic matter, thus producing an organic mix that is very resistant to further microbial or enzymatic attack. The butane may be injected intermittently to create feeding/starvation cycles within the microbial community.

Butane enrichment increases the numbers of butane oxidizers in soil. Due to a high diversity among this type of bacteria, it is believed that butane or alkane enrichment will provide enhanced benefits to plant development and growth. Some members of this community such as *Aeromonas caviae*, *Stenotrophomonas maltophilia*, *Micrococcus varians*, *Aureobacterium esteroaromaticum*, *Aureobacterium barkeri*, *Rhodococcus fascians*, *Nocardia paradoxus*, *Comamonas acidovorans* and *Pseudomonas aeruginosa*, play a major role in the heterotrophic nitrification process. Thus, butane enrichment within the region of a plant rhizosphere may result in an increase in overall heterotrophic bacteria, a portion of which accelerate the heterotrophic nitrification process, thus providing overall benefits and accelerating plant growth.

Butane, as a gas, may be used to effectively stimulate plant or crop growth over a wide area, unlike the currently available products that are produced as powders or granular substances that are mixed with water. Butane is non-toxic. In fact, butane is a general-purpose food additive and is used in the food processing industry to extract vital oils and flavors from a variety of food sources, and is also used as an aerosol propellant for health care products that contact the skin.

While particular embodiments of this invention have been described above for purposes of illustration, it will be evident to those skilled in the art that numerous variations of the details of the described examples may be made without departing from the invention.

What is claimed is:

1. A method of enhancing plant growth comprising the step of:
   introducing an alkane and an oxygen-containing gas into a location adjacent to a plant, wherein the alkane and oxygen-containing gas stimulate growth of alkane-utilizing bacteria which enhance growth of the plant.

2. The method of claim 1, wherein the alkane is introduced intermittently.

3. The method of claim 1, further comprising the step of:
   introducing another gas with the alkane and the oxygen-containing gas.

4. The method of claim 1, further comprising the step of:
   introducing nutrients with the alkane.

5. The method of claim 1, wherein the alkane comprises a butane substrate.

6. The method of claim 5, wherein the butane substrate comprises at least about 10 weight percent butane.

7. The method of claim 5, wherein the butane substrate comprises at least about 50 weight percent butane.

8. The method of claim 5, wherein the butane substrate comprises at least about 90 weight percent butane.

9. The method of claim 5, wherein the butane substrate comprises at least about 99 weight percent n-butane.

10. The method of claim 5, wherein the butane substrate comprises at least one of n-butane and iso-butane.

11. The method of claim 5, wherein butane is the most prevalent compound of the butane substrate on a weight percent basis.

12. The method of claim 5, wherein the butane substrate stimulates the growth of butane-utilizing bacteria.

13. The method of claim 12, wherein the butane-utilizing bacteria includes at least one of:
   *Aeromonas caviae, Stenotrophomonas maltophilia, Micrococcus varians, Aureobacterium esteroaromaticum, Aureobacterium barkeri, Rhodococcus fascians, Nocardia paradoxus, Comamonas acidovorans* and *Pseudomonas aeruginosa.*

14. The method of claim 5, wherein the butane substrate stimulates the growth of butane-utilizing fungi.

15. The method of claim 14, wherein the fungi comprise mycorrhizal fungi.

16. The method of claim 1, wherein the alkane increases the amount of heterotrophic bacteria in the location adjacent to the plant.

17. The method of claim 16, wherein the heterotrophic bacteria accelerate a heterotrophic nitrification process.

18. The method of claim 1, wherein the alkane increases the amount of fungi, algae, protozoa, rotifers and other aerobic and/or anaerobic microbial populations in the location adjacent to the plant.

19. The method of claim 1, wherein the alkane increases the amount of at least one of: Spirochetes; Aerobic/Microaerophilic, motile, helical/vibroid, gram-negative bacteria; Nonmotile (or rarely motile), gram-negative bacteria; Gram-negative aerobic/microaerophilic rods and cocci; Facultatively anaerobic gram-negative rods; Gram-negative, anaerobic, straight, curved, and helical bacteria; Dissimilatory sulfate- or sulfur-reducing bacteria; Anaerobic gram-negative cocci; Anoxygenic phototrophic bacteria; Oxygenic phototrophic bacteria; Aerobic chemolithotrophic bacteria and associated organisms; Budding and/or appendaged bacteria; Sheathed bacteria; Nonphotosynthetic, nonfruiting gliding bacteria; the fruiting, gliding bacteria and the Myxobacteria; Gram-positive cocci; Endospore-forming gram-positive rods and cocci; Regular, nonsporing, gram-positive rods; Irregular, nonsporing, gram-positive rods; the mycobacteria; the actinomycetes; Nocardioform actinomycetes; Genera with multiocular sporangia; Actinoplanetes; Streptomycetes and related genera; Maduromycetes; Thermomonospora and related genera; Thermoactinomycetes; Genus Glycomyces, Genus Kitasatospira and Genus Saccharothrix; the Mycoplasmas—cell wall-less bacteria; the Methanogens; Archaeal sulfate reducers; Extremely halophilic, archaeobacteria (halobacteria); Cell wall-less archaeobacteria; and Extremely thermophilic and hyperthermophilic $S^0$-metabolizers in the location adjacent to a plant.

20. The method of claim 1, wherein the location contains soil or a soil-less plant growth medium.

21. The method of claim 1, wherein the plant is grown in an aquatic, hydroponic or aeroponic growing system.

22. A plant grown by the method of claim 1.

23. The method of claim 1, wherein the alkane and the oxygen-containing gas are introduced at the same time.

24. The method of claim 1, wherein the alkane and the oxygen-containing gas are introduced at different times.

25. The method of claim 1, wherein the oxygen-containing gas comprises air.

26. A system for enhancing plant growth comprising:
   means for introducing an alkane and an oxygen-containing gas into a location adjacent to a plant, wherein the alkane and oxygen-containing gas stimulate growth of alkane-utilizing bacteria which enhance growth of the plant.

27. The system of claim 26, wherein the alkane is introduced intermittently.

28. The system of claim 26, wherein another gas is introduced with the alkane and the oxygen-containing gas.

29. The system of claim 26, wherein nutrients are introduced with the alkane.

30. The system of claim 26, wherein the alkane comprises a butane substrate.

31. The system of claim 30, wherein the butane substrate comprises at least about 10 weight percent butane.

32. The system of claim 30, wherein the butane substrate comprises at least about 50 weight percent butane.

33. The system of claim 30, wherein the butane substrate comprises at least about 90 weight percent butane.

34. The system of claim 30, wherein the butane substrate comprises at least about 99 weight percent n-butane.

35. The system of claim 30, wherein the butane substrate comprises at least one of n-butane and iso-butane.

36. The system of claim 30, wherein butane is the most prevalent compound of the butane substrate on a weight percent basis.

37. The system of claim 26, wherein the means for introducing an alkane comprises a perforated tube.

38. The system of claim 26, wherein the alkane and the oxygen-containing gas are introduced at the same time.

39. The system of claim 26, wherein the alkane and the oxygen-containing gas are introduced at different times.

40. The system of claim 26, wherein the oxygen-containing gas comprises air.

41. A system for enhancing plant growth comprising:
   an alkane source;
   a source of oxygen-containing gas; and
   at least one injector in flow communication with the alkane source and the source of oxygen-containing gas, wherein at least a portion of the injector is positioned at a location adjacent to a plant to stimulate growth of alkane-utilizing bacteria which enhance growth of the plant.

42. The system of claim 41, wherein the alkane comprises a butane substrate including at least about 10 weight percent butane.

43. The system of claim 41, wherein the alkane comprises a butane substrate comprising at least about 50 weight percent butane.

44. The system of claim 41, wherein the alkane comprises a butane substrate comprising at least about 90 weight percent butane.

45. The system of claim 41, wherein the alkane comprises a butane substrate comprising at least about 99 weight percent n-butane.

46. The system of claim 41, wherein the alkane source comprises a butane cylinder.

47. The system of claim 46, wherein the butane cylinder is in flow communication with a source of pusher gas.

48. The system of claim 47, wherein the pusher gas comprises helium.

49. The system of claim 48, wherein the source of pusher gas comprises a helium cylinder.

50. The system of claim 41, wherein the alkane source comprises means for storing the butane substrate in liquid form.

51. The system of claim 50, wherein the butane substrate is supplied to the injector in liquid form.

52. The system of claim 41, wherein the alkane is supplied to the injector in gaseous form.

53. The system of claim 41, wherein the system comprises a plurality of additional injectors.

54. The system of claim 41, wherein the at least one injector comprises a fluid inlet at a proximal end thereof and a fluid outlet at a distal end thereof.

55. The system of claim 54, wherein the at least one injector comprises a plurality of dispersion openings at the distal end thereof.

56. The system of claim 41, further comprising at least one valve in flow communication between the alkane source and the at least one injector.

57. The system of claim 56, wherein the valve is in flow communication between a source of oxygen-containing gas and the at least one injector.

58. The system of claim 56, further comprising a controller for the at least one valve.

59. The system of claim 58, wherein the controller comprises means for periodically opening and closing the at least one valve.

60. The system of claim 59, wherein the controller comprises a timer.

61. The system of claim 41, wherein the same injector is in flow communication with both the alkane source and the source of oxygen-containing gas.

62. The system of claim 41, wherein the system comprises at least two of the injectors.

63. The system of claim 62, wherein one of the injectors is in flow communication with the alkane source and another one of the injectors is in flow communication with the source of oxygen-containing gas.

64. A system for enhancing plant growth comprising:
an alkane source in a cylinder;
a source of pusher gas in flow communication with the alkane source in the cylinder; and
at least one injector in flow communication with the alkane source, wherein at least a portion of the injector is positioned at a location adjacent to a plant.

65. A system for enhancing plant growth comprising:
an alkane source;
at least one injector in flow communication with the alkane source, wherein at least a portion of the injector is positioned at a location adjacent to a plant to stimulate growth of alkane-utilizing bacteria which enhance growth of the plant;
at least one valve in flow communication between the alkane source and the at least one injector;
a controller for periodically opening and closing the at least one valve; and
a timer for operating the controller.

* * * * *